(12) United States Patent
Dahl et al.

(10) Patent No.: US 7,402,716 B2
(45) Date of Patent: Jul. 22, 2008

(54) HYBRID CUBIC/HEXAGONAL DIAMONDOIDS

(75) Inventors: Jeremy E. Dahl, Palo Alto, CA (US); Robert M. Carlson, Petaluma, CA (US); Shenggao Liu, Hercules, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 11/006,570

(22) Filed: Dec. 8, 2004

(65) Prior Publication Data

US 2005/0209490 A1   Sep. 22, 2005

Related U.S. Application Data

(60) Provisional application No. 60/533,966, filed on Dec. 31, 2003.

(51) Int. Cl.
*C07C 13/28* (2006.01)
*C07C 7/00* (2006.01)

(52) U.S. Cl. ............................ 585/352; 585/16; 585/21; 585/800; 585/802; 585/803; 117/68; 117/69; 117/70

(58) Field of Classification Search .................. 585/352, 585/16, 21, 800, 802, 803; 117/68, 69, 70
See application file for complete search history.

(56) References Cited

U.S. PATENT DOCUMENTS

| | | | |
|---|---|---|---|
| 4,952,749 A * | 8/1990 | Alexander et al. | 585/803 |
| 5,300,188 A * | 4/1994 | Tessmer et al. | 216/81 |
| 6,844,477 B2 | 1/2005 | Dahl et al. | |
| 6,861,569 B2 | 5/2005 | Dahl et al. | |

| | | | |
|---|---|---|---|
| 2002/0188163 A1 * | 12/2002 | Dahl et al. | 585/800 |
| 2002/0193648 A1 * | 12/2002 | Dahl et al. | 585/21 |

FOREIGN PATENT DOCUMENTS

| WO | WO 2004/009577 A1 | 1/2004 |
|---|---|---|
| WO | WO 2004/010512 A2 | 1/2004 |

OTHER PUBLICATIONS

Ansell, Martin F., "Diamond Cleavage". Publication unknown (4 pages), no date available.
Badziag, R., et al. "Nanometre-sized diamonds are more stable than graphite", *Nature* 343:244-245 (1990).
Stew, Stephen E., "Diamond and graphite precursors", *Nature* 346:517 (1990).
Balaban, Alexandru T., "Systemic Classification and Nomenclature of Diamond Hydrocarbons—I", *Tetrahedron* 34:3599-3609 (1978).
D.M. Gruen "Nucleation of ultrananocrystalline diamond films", Chapter B2.2 from *Properties, Growth and Applications of Diamondoids*, M.H. Nazare and A.J. Neves, editors, published by INSPEC, pp. 303-312 (2001).
Kulish, Wihlhelm, "Nucleation of Diamond", *Deposition of Diamond-Like Superhard Materials*, Springer-Vertage, pp. 134-141 (1999).
Lifshitz, Y., et al., "The Mechanism of Diamond Nucleation from Energetic Species", *Science* 297:1531-1533 (2002).
Prawer, Steven, "The Wonderful World of Carbon", *Physics of Novel Materials*, Mukunda P. Das, editor, Canberra, Australia, pp. 205-234 (1999).
International Search Report from PCT/US04/43095 mailed Jan. 27, 2006.

* cited by examiner

*Primary Examiner*—Elizabeth D Wood
(74) *Attorney, Agent, or Firm*—Crowell & Moring LLP

(57) ABSTRACT

Novel compounds having a hybrid cubic/hexagonal diamond crystal structure are disclosed. Each of the four compounds have the stoichiometric formula $C_{26}H_{32}$ and a molecular weight of 344. The four compounds are contemplated to have a utility in diamond film nucleation.

12 Claims, 4 Drawing Sheets

HYBRID CUBIC/HEXAGONAL DIAMONDOIDS

This application claims priority to U.S. Provisional Patent Application 60/533,966, filed Dec. 31, 2003, which is incorporated herein by reference in its entirety.

BACKGROUND OF THE INVENTION

1. Field of the Invention

Embodiments of the present invention are directed to novel compounds comprising hybrid cubic/hexagonal diamondoids. More specifically, embodiments of the present invention are directed to four compounds, each of which exhibit both the cubic diamond structure and the hexagonal diamond structure.

2. State of the Art

There are two forms of the diamond crystal structure, one hexagonal, the other cubic. As discussed in *Carbon Molecules and Materials,* edited by R. Setton, P. Bernier, and S. Lefrant (Taylor and Francis Inc., London and New York, 2002), a new phase of carbon, the hexagonal phase, was found among the crystals of cubic diamond in an x-ray diffraction experiment of synthetic diamond carried out at pressures greater than 130 GPa. According to Setton et al., the hexagonal phase may be obtained from pyrocarbons that have been subjected to a compression perpendicular to the layers, followed by annealing at a temperature greater than 1300 K. Hexagonal diamond has the lattice cell parameters $a_{hexagonal}$= 2.52 Å=$a_{cubic}/\sqrt{2}$, =4.12 Å=$2c_{cubic}/\sqrt{3}$, and a $P6_3$/mmc space group. The density of hexagonal diamond is 3.51 g/cm3, which is the same as that in cubical diamond, and the position of the carbons is the same as the atomic positions in the wurtzite crystal structure. A hexagonal diamond crystal cage is shown in FIG. 1A, where only the carbon atom lattice sites have been shown (at the line intersections), and the hydrogen atoms have been omitted.

Also discussed in *Carbon Molecules and Materials* are the properties of cubic diamond. Cubic diamond has a space group of Fd3m, with the latice cell parameters $a_{cubic}=b_{cubic}=c_{cubic}=3.5597$ angstroms. Cubic diamond has 8 atoms per unit cell, and a density of 3.51 g/cm$^3$. The carbon atoms of cubic diamond are all in the chair conformation, as illustrated in FIG. 1B, where again, only the carbon atom lattice sites have been shown.

Cubic diamondoids are known in the art. What has not been disclosed are diamondoids that contain both the cubic and hexagonal forms of the diamond crystal structure. Each of the four hybrid cubic/hexagonal compounds of the present invention have the stoichiometric formula $C_{26}H_{32}$ and a molecular weight of 344.

SUMMARY OF THE INVENTION

Embodiments of the present invention are directed to novel compounds comprising hybrid cubic/hexagonal diamondoids. More specifically, embodiments of the present invention are directed to four compounds, each of which exhibit both the cubic diamond structure and the hexagonal diamond structure.

It is contemplated that a utility of the present cubic/hexagonal hybrid diamondoids is the nucleation of diamond films.

The combination of boat and chair configurations of the cage faces of the diamond structure of the present embodiments are contemplated to facilitate the nucleation of a diamond film.

DETAILED DESCRIPTION OF THE INVENTION

Structures

The four compounds of the present invention have a molecular weight of 344, and are fully saturated polycyclic hydrocarbons that contain a mixture of hexagonal and cubic diamond crystal structures. The hexagonal portion of these four 344 molecular weight, $C_{26}H_{32}$ hybrid compounds consist of the two basic hexagonal dimer units, shown individually in FIGS. 2A and 2B, respectively.

Figure 1A:
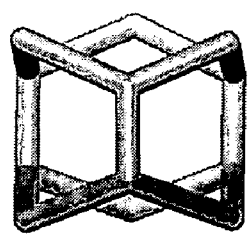
FIGS. 1A and 1B illustrate cage structures that are a part of the hexagonal and cubic diamond crystal structures, respectively.
Figure 1B:
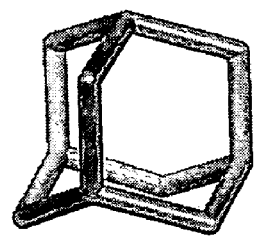
Figure 2A:
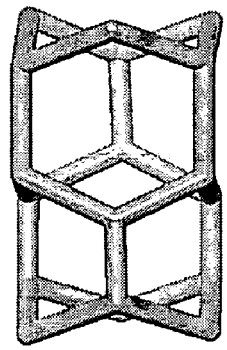
FIG. 2A illustrates the hexagonal diamond crystal cage unit of the first two 344 molecular weight hybrid molecules.

In the case of the FIG. 2A hexagonal dimer unit, only two faces (21 and 22) are available for the attachment of the cubic units. Shown in FIG. 2A is the hexagonal diamond crystal dimer cage unit contained in 344 hybrid compounds depicted in FIGS. 3 and 4. Reference numerals 21 and 22 in FIG. 2A point to the two hexagonal cage faces where cubic cages can potentially face-fuse in order to generate the FIG. 3 and FIG. 4 structures. To generate the compound in FIG. 3, a first cubic cage attaches (face fuses) to the cage face 21, and a second cubic cage attaches (face fuses) to the cage face 22. In an alternate way of attaching two cubic cages to the structure shown in FIG. 2A, thus generating the compound in FIG. 4, a first cubic cage attaches (face fuses) to the cage face 21 (as before), but the second cubic cage attaches to the first cubic cage already attached, instead of attaching to hexagonal face 22. This second hexagonal face 22 remains open.

The hexagonal cage dimer shown in FIG. 2A is symmetrical such that the attachment of a single cubic diamond crystal cage to either face 21, 22 generates identical structures. To create the second of the two hybrids from FIG. 2A, the second cubic diamond must be face-fused to one of the three available cubic cage faces. Again, due to the high symmetry, attachment of the second cubic cage to any of the three available cubic faces produces identical structures.

Figure 2B:
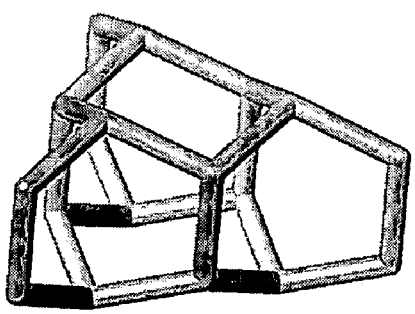
FIG. 2B illustrates the hexagonal diamond crystal cage unit of the second two 344 molecular weight hybrid molecules.
Figure 3A:
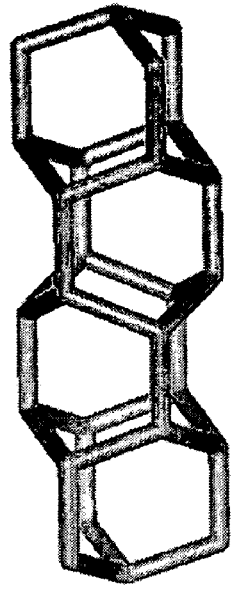
FIG. 3A shows a perspective structure of the first 344 molecular weight hexagonal-cubic hybrid compound.
Figure 4A:
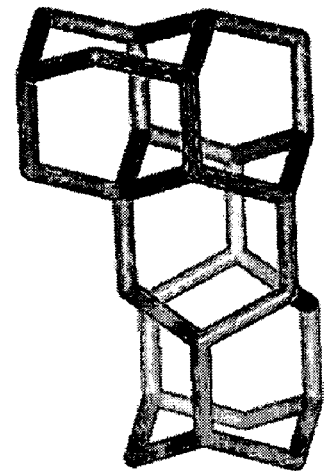
FIG. 4A shows a perspective structure of the second 344 molecular weight hexagonal-cubic hybrid compound.
Figure 5A:
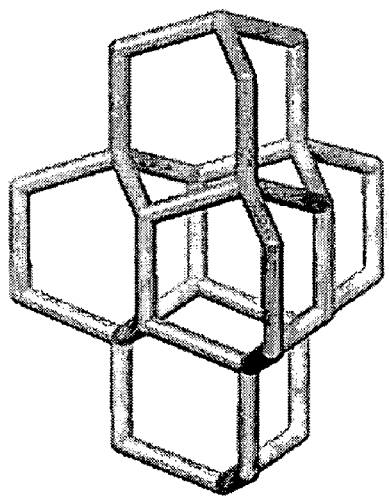
FIG. 5A shows a perspective structure of the third 344 molecular weight hexagonal-cubic hybrid compound.

Shown in FIG. 2B is the hexagonal diamond crystal dimer cage unit contained in 344 hybrid compounds depicted in FIGS. 5 and 6. Similar to the situation for FIG. 2A, the FIG.

2B hexagonal cage dimer has only two cage faces 23, 24 available for the attachment of a cubic unit. The third 344 molecular weight hybrid contains this hexagonal dimer unit with a cubic diamond crystal cage attached to each of the two available hexagonal faces 23, 24, thus generating the structure shown in FIG. 5A. Because the hexagonal dimer shown in FIG. 2B is symmetrical, attaching cubic cages to the faces 23, 24 in either order generates identical structures.

Figure 6A:
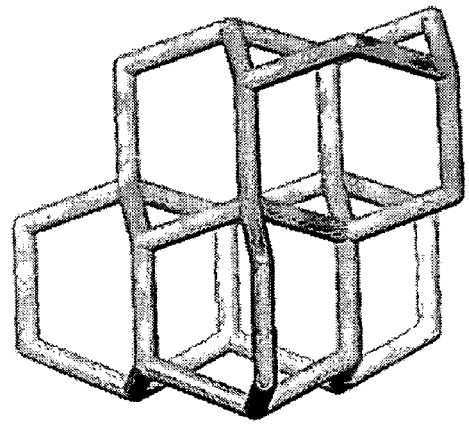
FIG. 6A shows a perspective structure of the fourth 344 molecular weight hexagonal-cubic hybrid compound.
Figure 3B:
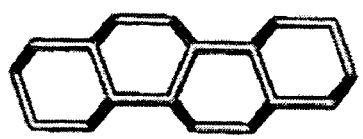
FIGS. 3B-D illustrate side, end, and top views of the first 344 molecular weight hybrid structure.
Figure 3C:
Figure 3D:
Figure 4B:
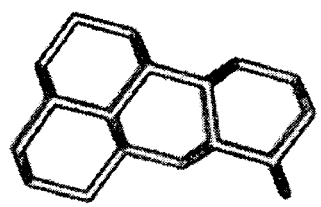
FIGS. 4B-D illustrate side, end, and top views of the second 344 molecular weight hybrid structure.
Figure 4C:
Figure 4D:
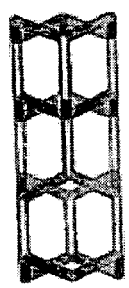
Figure 5B:
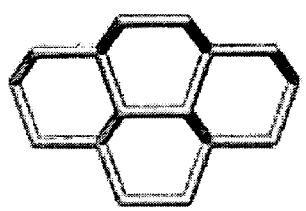
FIGS. 5B-D illustrate side, end, and top views of the third 344 molecular weight hybrid structure.
Figure 5C:
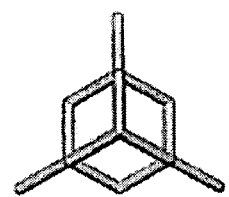
Figure 5D:
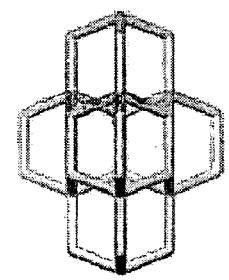
Figure 6B:
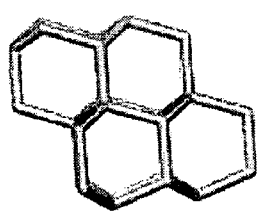
FIGS. 6B-D illustrate side, end, and top views of the fourth 344 molecular weight hybrid structure.
Figure 6C:
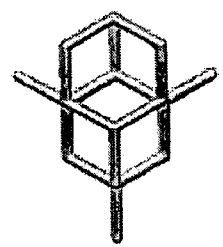
Figure 6D:
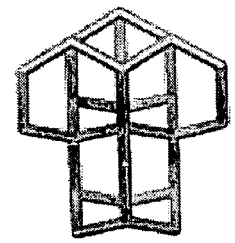

The fourth 344 molecular weight hybrid that may be generated from the hexagonal dimer of FIG. 2B is shown in FIG. 6A. In this case, the second cubic cage is face-fused to one of the faces of the first (already attached) cubic cage. Again, due to the high symmetry of the FIG. 2B hexagonal dimer with a cubic cage attached to either face 23, 24, attachment of a cubic cage to any of the three available faces of the first attached cubic face produces identical faces.

In an alternative description of the various embodiments, the number of faces that correspond to a particular type of cage contained within each hybrid may be tabulated. For example, the hybrid depicted in FIG. 3 contains two four-faced cages and two five-faced cages. This is the same situation for the hybrid depicted in FIG. 4. The hybrid depicted in FIG. 5 contains two four faced cages, one five-faced cage, and three three-faced cages. The hybrid molecule described in FIG. 6 may be described in the same manner. See Table 1:

TABLE 1

Number of x-faced cages in each of the hybrid molecules

| hybrid molecule | number cages with 4 faces | number cages with 5 faces | number cages with 3 faces |
| --- | --- | --- | --- |
| FIG. 3 | 2 | 2 | 0 |
| FIG. 4 | 2 | 2 | 0 |
| FIG. 5 | 2 | 1 | 3 |
| FIG. 6 | 2 | 1 | 3 |

Another way in which the four 344 molecular weight hybrid molecules may be described is by tabulating whether or not the cages in each of the hybrids are in the chair or boat conformations, regardless of whether they are positioned in the 4-, 3-, or 5-faced cages. Again, the 4-faced cages are part of the cubic diamond structure, and the 3-faced and 5-faced structures are a part of the hexagonal diamondoid structure. This information may be seen in Table 2:

TABLE 2

Number of cages in the chair or boat configuration

|  | Cubic | Hexagonal | Hexagonal |
| --- | --- | --- | --- |
| Number of faces per cage unit | 4 | 3 | 5 |
| Types of faces | All 4 are chair | All 3 are boat | 3 are boat; 2 are chair |

Another way in which the four 344 molecular weight hybrid molecules may be described is by tabulating the number of secondary, tertiary, or quaternary carbons in each molecule. Each of the four hybrid molecules has the stoichiometric formula $C_{26}H_{32}$, and for the 26 carbons of each molecule the number of secondary, tertiary, or quaternary carbons varies, as seen in Table 3:

TABLE 3

Number secondary, tertiary, and quaternary carbons

| hybrid molecule | secondary carbons | tertiary carbons | quaternary carbons |
| --- | --- | --- | --- |
| FIG. 3 | 6 | 20 | 0 |
| FIG. 4 | 7 | 18 | 1 |
| FIG. 5 | 12 | 8 | 6 |
| FIG. 6 | 10 | 12 | 4 |

Having described the four members of the 344 molecular weight hybrid cubic hexagonal structures in several different ways, this disclosure will now turn to methods of isolation.

Isolation

Figure 7:
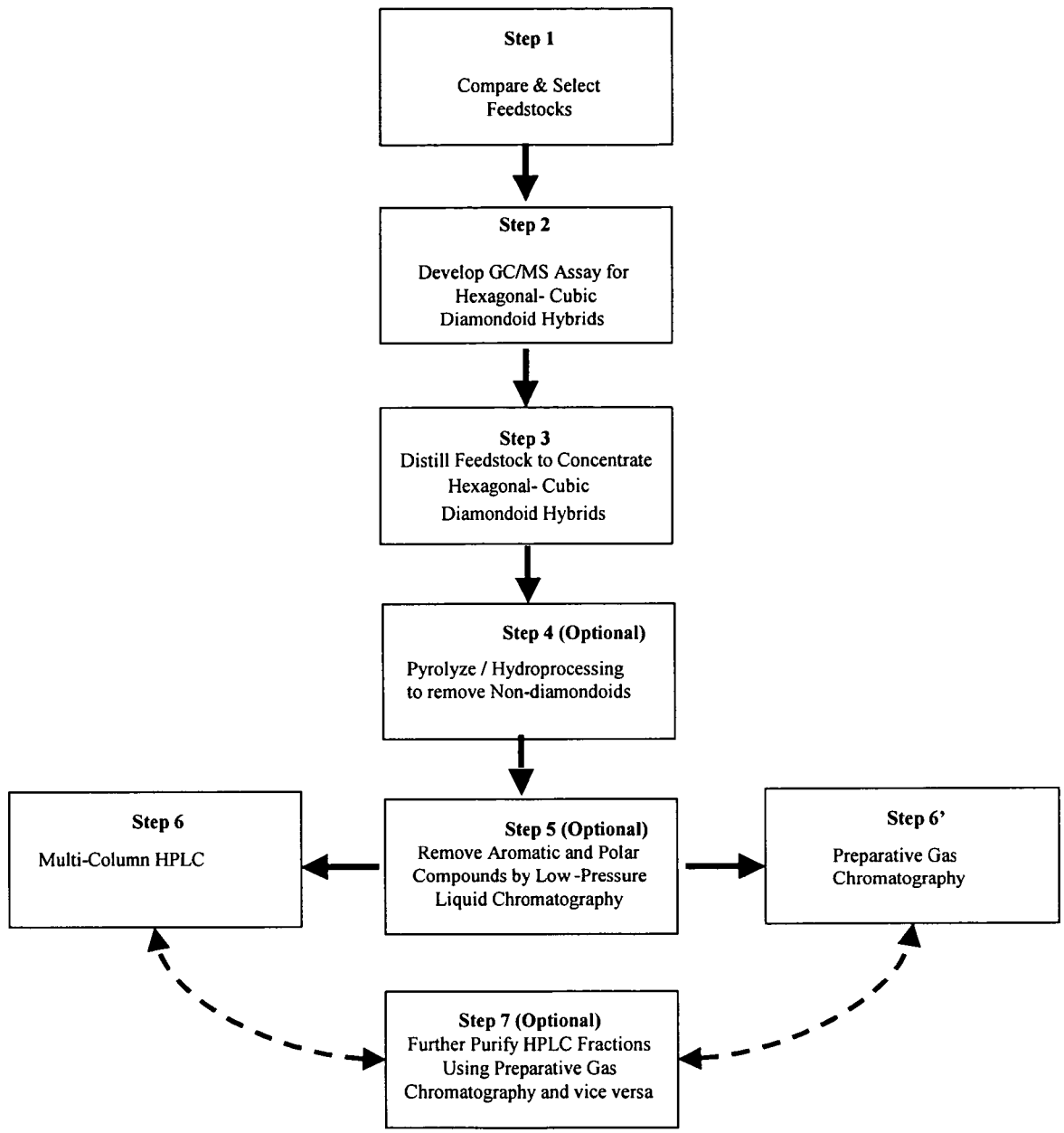
FIG. 7 shows an exemplary method by which the hybrid cubic/hexagonal diamondoids of the present invention may be isolated.

Petroleum feedstocks must be compared and selected prior to isolation of hexagonal-cubic hybrid diamondoids. Once a feedstock has been selected, a GCMS assay for the 344 MW hexagonal-cubic hybrid diamondoids must be developed which identifies the molecular ion and gas chromatographic retention times. Referring to FIG. 7, the initial isolation step involves distillation to concentrate target species followed using the assay. Distillate fractions are then pyrolyzed or hydroprocessed to remove nondiamondoid hydrocarbons.

Remaining aromatic and polar compounds can be removed from pyrolysates by liquid chromatography and hexagonal-cubic hybrid diamondoids can be isolated either by preparative gas chromatography and/or high performance liquid chromatography (HPLC). Once isolated and crystallized, structures may be identified by x-ray diffraction.

It is contemplated that a utility of the present cubic/hexagonal hybrid diamondoids is the nucleation of diamond films.

The combination of boat and chair configurations of the cage faces of the diamond structure of the present embodiments are contemplated to facilitate the nucleation of a diamond film.

Many modifications of the exemplary embodiments of the invention disclosed above will readily occur to those skilled in the art. Accordingly, the invention is to be construed as including all structure and methods that fall within the scope of the appended claims.

What is claimed is:

1. A composition of isolated hybrid cubic/hexagonal diamondoids comprising an isolated hybrid cubic/hexagonal diamondoid having the following structure:

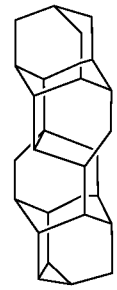

wherein the hybrid cubic/hexagonal diamondoid has a molecular weight of 344 and the stoichiometric formula $C_{26}H_{32}$.

2. A composition of isolated hybrid cubic/hexagonal diamondoids comprising an isolated hybrid cubic/hexagonal diamondoid having the following structure:

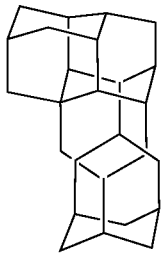

wherein the hybrid cubic/hexagonal diamondoid has a molecular weight of 344 and the stoichiometric formula $C_{26}H_{32}$.

3. A composition of isolated hybrid cubic/hexagonal diamondoids comprising an isolated hybrid cubic/hexagonal diamondoid having the following structure:

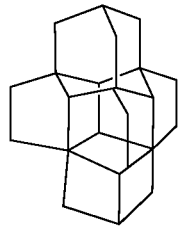

wherein the hybrid cubic/hexagonal diamondoid has a molecular weight of 344 and the stoichiometric formula $C_{26}H_{32}$.

4. A composition of isolated hybrid cubic/hexagonal diamondoids comprising an isolated hybrid cubic/hexagonal diamondoid having the following structure:

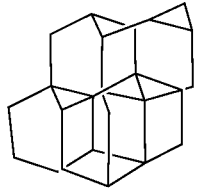

wherein the hybrid cubic/hexagonal diamondoid has a molecular weight of 344 and the stoichiometric formula $C_{26}H_{32}$.

5. A method of nucleating a diamond film, wherein the film is nucleated by the composition of claim 1.

6. A method of nucleating a diamond film, wherein the film is nucleated by the composition of claim 2.

7. A method of nucleating a diamond film, wherein the film is nucleated by the composition of claim 3.

8. A method of nucleating a diamond film, wherein the film is nucleated by the composition of claim 4.

9. A diamond film produced by the method of claim 5.

10. A diamond film produced by the method of claim 6.

11. A diamond film produced by the method of claim 7.

12. A diamond film produced by the method of claim 8.

* * * * *